United States Patent
Lachner et al.

(10) Patent No.: US 10,062,179 B2
(45) Date of Patent: Aug. 28, 2018

(54) AUTO-CALIBRATION OF PROBABILISTIC TRACKING PARAMETERS FOR DTI FIBRE TRACTOGRAPHY AND COMPILATION OF TRACT PROBABILITY COMPARISON SCALES

(71) Applicant: Brainlab AG, Munich (DE)

(72) Inventors: Rainer Lachner, Munich (DE); Balint Varkuti, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/508,794

(22) PCT Filed: Sep. 16, 2014

(86) PCT No.: PCT/EP2014/069697
§ 371 (c)(1),
(2) Date: Mar. 3, 2017

(87) PCT Pub. No.: WO2016/041577
PCT Pub. Date: Mar. 24, 2016

(65) Prior Publication Data
US 2018/0018790 A1 Jan. 18, 2018

(51) Int. Cl.
*G06K 9/00* (2006.01)
*G06T 7/73* (2017.01)
(Continued)

(52) U.S. Cl.
CPC .............. *G06T 7/75* (2017.01); *A61B 5/0042* (2013.01); *A61B 5/055* (2013.01); *A61B 5/4064* (2013.01);
(Continued)

(58) Field of Classification Search
CPC . G06T 2207/30016; G06T 2207/10092; A61B 5/055; A61B 5/4064; G01R 33/56341
(Continued)

(56) References Cited

U.S. PATENT DOCUMENTS 7,881,878 B2    2/2011  Burrus et al.
8,340,376 B2 *  12/2012  Simon .............. G01R 33/56341
                                                        382/128
(Continued)

FOREIGN PATENT DOCUMENTS

EP        2141506 A2    1/2010
WO    2004051568 A1    6/2004
(Continued)

OTHER PUBLICATIONS

Donald J. Hagler Jr., et al. "Automated White-Matter Tractography Using a Probabilistic Diffusion Tensor Atlas: Application to Temporal Lobe Epilepsy", Human Brain Mapping, 30:1535-1547 (2009).
(Continued)

*Primary Examiner* — Charlotte M Baker
(74) *Attorney, Agent, or Firm* — Middleton Reutlinger (57) ABSTRACT

1. A medical data processing method of determining information describing the probable position of a neural fiber in a patient's brain, the method comprising the following steps which are constituted to be executed by a computer: a) acquiring patient-specific medical image data describing the brain of the patient; b) acquiring atlas data defining an image-based model of a human brain; c) determining, based on the patient-specific medical image data and the atlas data, seed region data describing seed regions (A, B) in the patient-specific medical image data in which the ends of neural fibers of the patient's brain may be located; d) determining, based on the patient-specific medical image data and the seed region data, neural fiber tract data describing a plurality of potential tracts (T1, T2, T3) which a specific neural fiber may take through the patient's brain; e) determining, based on the atlas data and the neural fiber tract
(Continued)

data, a figure of merit for each one of the potential tracts (T1, T2, T3).

17 Claims, 3 Drawing Sheets

(51) Int. Cl.
```
G06T 7/246      (2017.01)
G06T 7/143      (2017.01)
A61B 5/00       (2006.01)
A61B 5/055      (2006.01)
G06T 7/11       (2017.01)
G01R 33/48      (2006.01)
G06T 7/60       (2017.01)
```

(52) U.S. Cl.
CPC ............... *G06T 7/11* (2017.01); *G06T 7/143* (2017.01); *G06T 7/251* (2017.01); *A61B 2576/026* (2013.01); *G01R 33/4806* (2013.01); *G06T 7/60* (2013.01); *G06T 2207/10092* (2013.01); *G06T 2207/20076* (2013.01); *G06T 2207/20128* (2013.01); *G06T 2207/20156* (2013.01); *G06T 2207/20221* (2013.01); *G06T 2207/30016* (2013.01); *G06T 2207/30024* (2013.01); *G06T 2207/30241* (2013.01); *G06T 2210/41* (2013.01)

(58) Field of Classification Search
USPC ............ 382/103, 128; 600/424, 411; 607/45
See application file for complete search history.

(56) References Cited

U.S. PATENT DOCUMENTS 8,532,741 B2 *   9/2013   Heruth ............... A61B 19/5244
                                                        600/411
2010/0135560 A1   6/2010   Embleton et al.

FOREIGN PATENT DOCUMENTS

| WO | 2011119935 A2 | 9/2011 |
| WO | 2012041364 A1 | 4/2012 |
| WO | 2014023350 A1 | 2/2014 |

OTHER PUBLICATIONS

European Patent Office, International Search Report and Written Opinion for PCT/EP2014/069697 dated Mar. 24, 2016.

Anastasia Yendiki, et al. "Automated probalistic reconstruction of white-matter pathways in health and disease using an atlas of the underlying anatomy", Frontiers in Neuroinformatics, vol. 5, Jan. 1, 2011, p. 23.

Ping-Hong Yeh, et al. "Diffusion Tensor Imaging and Its Application to Traumatic Brain Injury: Basic Principles and Recent Advances", Open Journal of Medical Imaging, vol. 2, No. 4, Jan. 1, 2012, pp. 137-161.

* cited by examiner

AUTO-CALIBRATION OF PROBABILISTIC TRACKING PARAMETERS FOR DTI FIBRE TRACTOGRAPHY AND COMPILATION OF TRACT PROBABILITY COMPARISON SCALES

The present invention is directed to a medical data processing method of determining information describing the probable position of a neural fibre in a patient's brain, a computer running that program and a system comprising that computer.

Currently, software packages that perform probabilistic tractography—in combination with the outlined calibration/interpretation aids—are not available. Open-source systems such as FSL, Freesurfer, SPM, MedInria, DTI Studio and others do offer probabilistic tracking but without a critical system for parameter calibration and probability scaling.

The TRACULA system (available at http://freesurfer.net/fswiki/Tracula) for example utilizes atlas priors for tracking, but not the end described in the present invention.

The inventors do not know of one method or paradigm that allows for optimal parameter selection for probabilistic tractography and at the same time execution of a method to provide a comparison scale for probability that are based on the dataset at hand. Methods for identification/segmentation of known anatomy (specifically for white matter) are known to exist though—such as registration of individual patient data with the ICBM-DTI-81 white matter atlas.

In probabilistic tractography it is a challenge to choose tracking parameters such as number of random walks, maximum curvature, revisit & loop setting, mask thresholding and many more in a manner that produces clinically interpretable results. The trade-off here is between choosing too conservative settings that do not provide a real advantage over deterministic tractography, versus too loose settings where fibres are tracked/identified which do not really exist. Furthermore, the probability outputs of such procedures are not normed to a scale that would be comparable across subjects or measurement time points, hence making clinical interpretation (differing between whether there is a fibre or whether there is no fibre) difficult.

A key problem here is that probabilistic methods do not necessarily give fibres as an output but rather probability fields, which can be visualized as a heatmap with a few localized bright/intense zones of high probability and many dimmer zones with lower probability values (corresponding to less likely fibre connections). However, these outputs are not scaled so a systematic comparison within or between subjects is challenging and necessarily constricted to an ordinal-scale (more or less) comparison logic.

A problem to be solved by the present invention therefore is to provide a reliable method for determining the probability for a potential fibre tract to resemble a real fibre tract.

This problem is solved by the subject-matter of any appended independent claim. Aspects and embodiments of the present invention are disclosed in the following. Different features of the invention can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

The present invention is designed to be used for example with the new Fibretracking Element software which is the successor to the—clinically broadly used—iPlan Fibretracking software product supplied by Brainlab AG. In this context, the integration of the invention would allow the user to perform probabilistic tractography with the added value of receiving results with a reliability that is as interpretable as currently available deterministic fibre tracking results.

Exemplary Short Description of the Present Invention

In the following, a short description of the specific features of the present invention is given which shall not be understood to limit the invention only to the features or a combination of the features described in this section.

The present invention relates for example to a method for intra-subject/session intra-dataset calibration of tracking parameters and/or for obtaining probability scaling information for interpretation of results. First, known anatomical zones in cerebral white matter are identified. Then, information regarding features of such zones is identified. Tracking parameters are relaxed iteratively until known crossings of neural fibres are overcome and/or complex tracts are reconstructed. Finally, the resulting probability histograms are used as a basis interpretation of probabilistic results within known/identified feature classes of neural fibre tracts.

General Description of the Present Invention

In this section, a description of the general features of the present invention is given for example by referring to possible embodiments of the invention.

In one aspect, the invention is directed to a medical data processing method of determining information describing (for example defining) the probable position (for example, at least one of position and orientation) of a neural fibre in a patient's brain. The term of position encompasses at least one of location and orientation. The method comprises for example the following steps a) to e) which are constituted to be executed by a computer:

a) acquiring patient-specific medical image data describing (for example defining) the brain of the patient (for example, an image of the brain of the patient);
b) acquiring atlas data describing (for example defining) an image-based model of a human brain;
c) determining, based on the patient-specific medical image data and the atlas data, seed region data describing (for example defining) seed regions in the patient-specific medical image data in which the ends of neural fibres of the patient's brain may be located;
d) determining, based on the patient-specific medical image data and the seed region data, neural fibre tract data describing (for example defining) a plurality of potential tracts which a specific neural fibre may take through the patient's brain;
e) determining, based on the atlas data and the neural fibre tract data, a figure of merit for each one of the potential tracts.

According to an embodiment, the patient-specific medical image data is for example suitable for identifying neural fibres in the brain of the patient and for example is medical image data which has been generated at least partly by diffusion tensor imaging (DTI).

The aforementioned ends of neural fibres are open ends of the neural fibres. The term "end of a neural fibre" therefore encompasses are at least one of a start point and an end point of a neural fibre. The end point of a neural fibre is defined to lie closer to the target of nervous stimulus transmission then the start point.

According to an embodiment, the atlas data comprises for example tissue class information describing (for example defining) the image appearance, for example a colour value, of specific body tissue in the imaging modality which is used to generate the patient-specific medical image information.

The colour value can be a grey value, but also polychrome values are possible as a colour value.

The atlas data defines an atlas (representing for example a universal atlas which may be applicable to a plurality of different types of patients) which serves as a basis for parcellating the white brain matter into functional zones which correspond to standard tracts such as the corpus callosum, the cortico-spinal tract (CST) or the optic radiation. The parcellation logic utilizes a table within which known properties of the standard tracts are captured (including for example information about the length of a fibre, information describing whether it is very curvy or very straight and/or whether it crosses another tract or not). The atlas therefore contains multiple zones/tracts for one property constellation in order to be able to choose fallback regions in the case of pathologically altered brains where a zone cannot be found (e.g. if left CST is not available use right, if right is not available use longitudinal fascicle as long straight tract).

According to an embodiment, the seed region data is determined by determining a transformation between the atlas data and the patient-specific medical image data. The term of transformation denotes for example a mapping (such as a coordinate mapping) which can be embodied by a linear function (for example, a multiplication with a mapping matrix). The transformation is determined for example by performing an image fusion between the atlas data and the patient-specific medical image data. Furthermore, the seed region data is determined based on for example determining the position of white brain matter in the patient-specific medical image data based on the transformation. The seed regions are for example at least two spatially disjunct and individually coherent seed regions and are constituted for example by white brain matter. The position of the white brain matter in the image-based model is determined for example by segmenting the image-based model for tissue class information defining white brain matter.

According to an embodiment, the positions of a plurality of spatially disjunct and individually coherent regions of white brain matter are determined in the patient-specific medical image data based on the transformation. The coherent regions of white brain matter are sorted according to the geometric properties (for example, at least one of fibre length and curvedness or curvature) of model neural fibre tracts in the image-based model connecting regions of white brain matter and according to the probability of the respective model neural fibre tracts to contain fibre crossings. For example, regions of white brain matter having a high priority in the sorting are selected as the seed regions. The curvedness of a neural fibre is understood to be a quantitative measure for the geometric linearity of the fibre tract. A fibre tract having a low curvedness will have a geometry more similar to a straight line, a fibre tract having a high curvedness will in contrast to a straight line have more curved sections, i.e. will undergo a plurality of positional direction changes (i.e. orientation changes) along its lengthwise extension.

According to an embodiment, the neural fibre tract data is determined by selecting exactly one of the seed regions as a start region and applying a random walk algorithm to the patient-specific medical image data which as a result generates a plurality of random walks. For example, each random walk out of the plurality of random walks is designed to start at the start region and to lead to another one of the seed regions which serves as a desired end region for the random walk.

According to an embodiment, the initial values of the random walk algorithm are determined based on the sorting of the coherent regions, for example based on the sorting of physical parameters of pre-tracked white brain matter structures such as their length, curvedness, anatomical similarity and/or probability for containing crossing fibres. For example, the initial values of the random walk algorithm are determined so as to optimally represent the ideal conditions under which said reference coherent region was optimally reconstructed. The anatomic similarity may for example be derived from e.g. a comparison of a specific brain region with a paired region on the contralateral side of the brain.

According to an embodiment, the random walk algorithm is initiated at a specific position ($s\_0$) in the start region with a predetermined step size (d). Every direction ($v\_i$) in which each one of the N−1 total steps of the random walk proceeds from the current position ($s\_i$, where n=0, 1, 2, . . . , N; and N−1 is the length of the random walk) currently considered by the random walk algorithm is determined based on the patient-specific medical image data. For example, it is determined from a diffusion tensor determined from the patient-specific medical image data for the current position.

According to an embodiment, every direction in which the random walk proceeds is determined based on determining a probability of that direction being a valid direction for propagating the random walk, the probability being determined based on the result of an analysis of the geometry, for example of at least one of size and shape, of a diffusion tensor determined from the patient-specific medical image data for the current position According to an embodiment, each one of the plurality of random walks which does not end in the end region is excluded from further data processing, for example is discarded. For example, each one of the plurality of random walks which ends in the end region is considered for further data processing, so it may for example be said to constitute a valid random walk.

According to an embodiment, the figure of merit is determined based on the difference in curvature, for example by acquiring curvature difference threshold data about a curvature difference threshold describing (for example defining) a predetermined, for example acceptable, difference in curvature. The curvature difference threshold is then compared to the determined difference in curvature; this is done for example by determining whether the determined difference in curvature is greater or less than or equal to the curvature difference threshold. The figure of merit is for example a measure defining the suitability of the determined potential tract as a fibre tract. In other words, it defines a probability for the potential tract representing a (real) fibre tract.

According to an embodiment, the atlas data comprises fibre tract model information describing (for example defining) the position of model neural fibre tracts in the image-based model, and wherein the fibre tract model information is compared based on at least one physical parameter of pre-tracked white brain matter structures such as their length, curvedness, anatomical similarity, to the corresponding random-walk based fibre.

According to an embodiment, the curvature of the core (which is represented for example by the main trunk) of at least one of the model neural fibre tracts in the image-based model is the curvature with respect to a non-curved (for example straight) virtual line between the end points of the tract. For example, the curvature of the random walks is a calculated similarly with respect to the non-curved virtual line between the target termination area of the random walks.

According to an embodiment, the method comprises determining, based on the figure of merit, the potential fibre tract as being a fibre tract which is suitable for, as an example, planning a medical procedure which the patient shall be subjected to. The identified fibre tract can be used in the context of treatment planning (e.g. trajectory planning) or be an item of analysis for e.g. repeated DTI scans of the patient to determine changes in white matter morphology that might constitute biomarkers for certain diseases.

In another aspect, the invention also relates to a program which, when running on a computer, causes the computer to perform one or more or all of the method steps described herein. In a further aspect, the invention relates to a program storage medium on which the program is stored (for example in a non-transitory form) and/or to a computer comprising said program storage medium. In an even further aspect, the invention relates to a (physical, for example electrical, for example technically generated) signal wave, for example a digital signal wave, carrying information which represents the aforementioned program, which comprises code means which are adapted to perform any or all of the method steps described herein.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines and/or represents and/or is) for example a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, for example a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the enclosed figures which represent a specific embodiment of the invention. The scope of the invention is not however limited to the specific features disclosed in the context of the figures, wherein.

Figure 1:
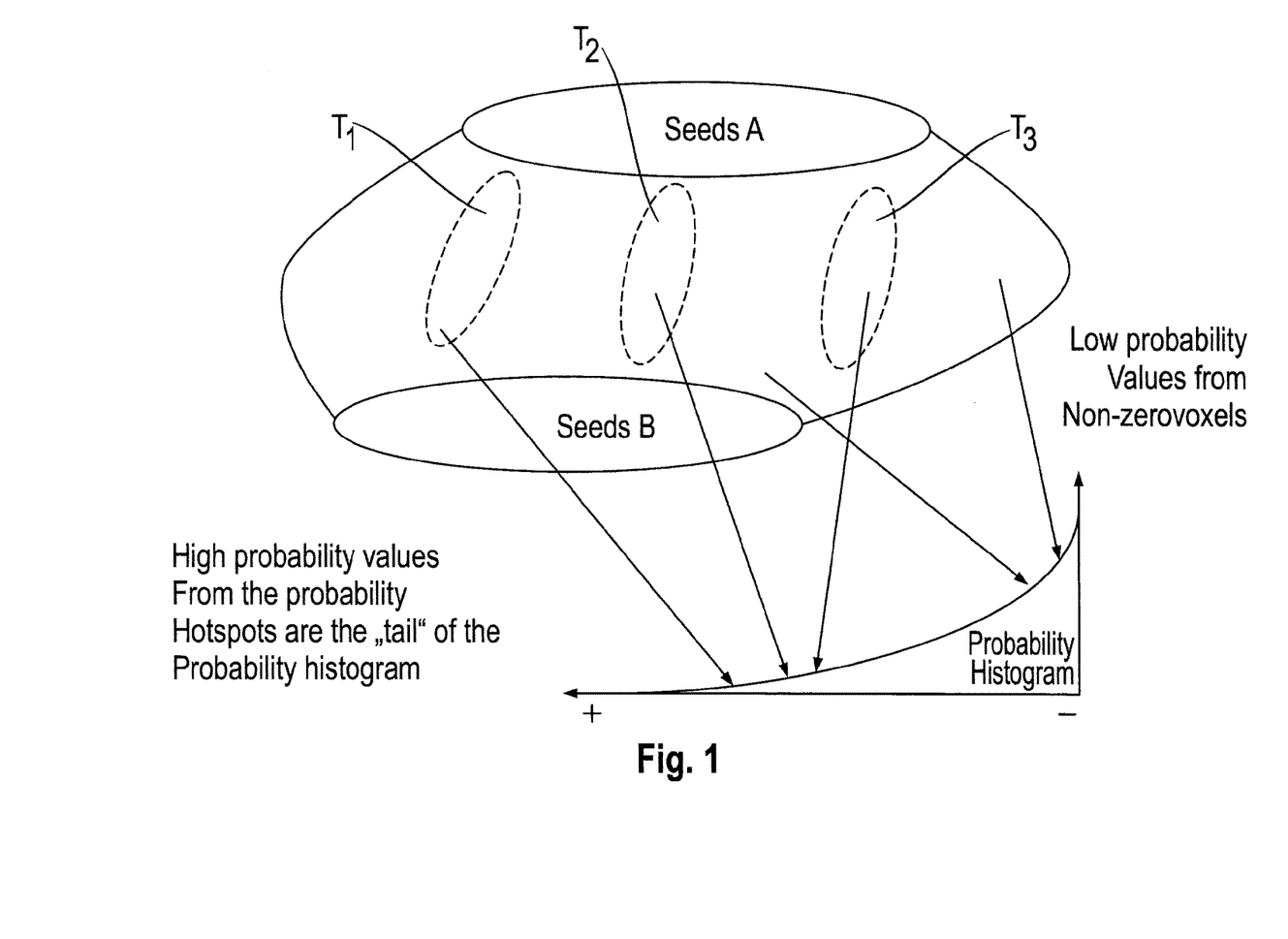
FIG. 1 is an illustration of probability histograms obtained from probabilistic tractography outputs.

FIG. 1 contains a probability histogram for certain determined potential fibre tracts running between seed regions A and B representing the start and end points, respectively, of the fibre tracts. The space between two seed regions contains usually many non-zero low-probability values representing unlikely pathways connecting the two seed regions, and a number of islands/zones of probability ($T_1$, $T_2$ and $T_3$) within which probability values can be found that when compared along the present probability value histogram determine which one of them is most likely to represent the core region of a probable fibre connection between the aforementioned seeds.

Figure 2:
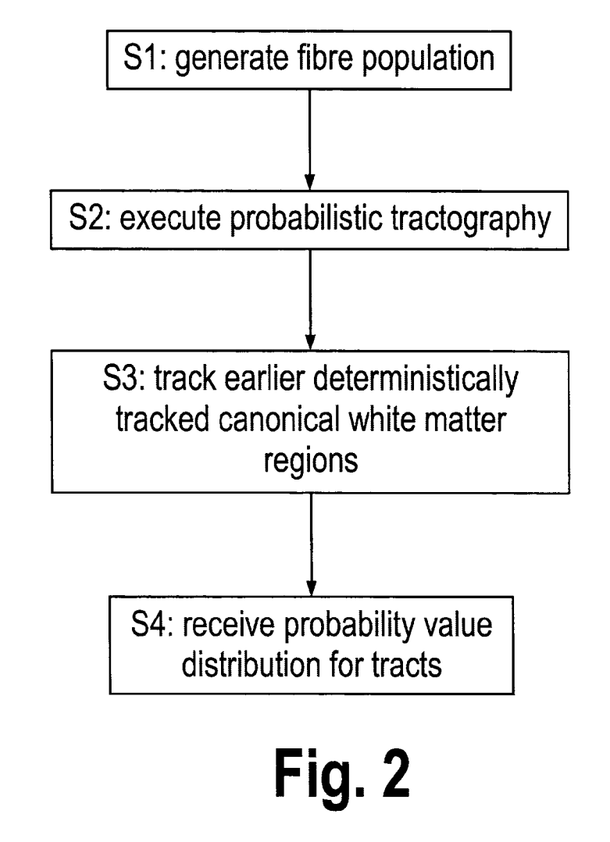
FIG. 2 is a flow diagram describing the method in accordance with the invention.

FIG. 2 describes the invention in terms of a stepwise procedure for determining the probability distribution shown in FIG. 1.

In step S1 deterministic tractography (e.g. the FACT algorithm) is employed to generate a fibre population which is considered a reliable estimate of fibre tracts which are not challenging to track (e.g. straight uncurving fibre bundles). The visitation masks for these deterministic tractography results are saved.

In step S2 probablistic tractography is conducted utilizing first conservative settings (low number of random walks, low curvature, strict termination criteria). This probabilistic tractography is specifically conducted in regions of the brain where crossing fibres are known to exist.

Figure 3:
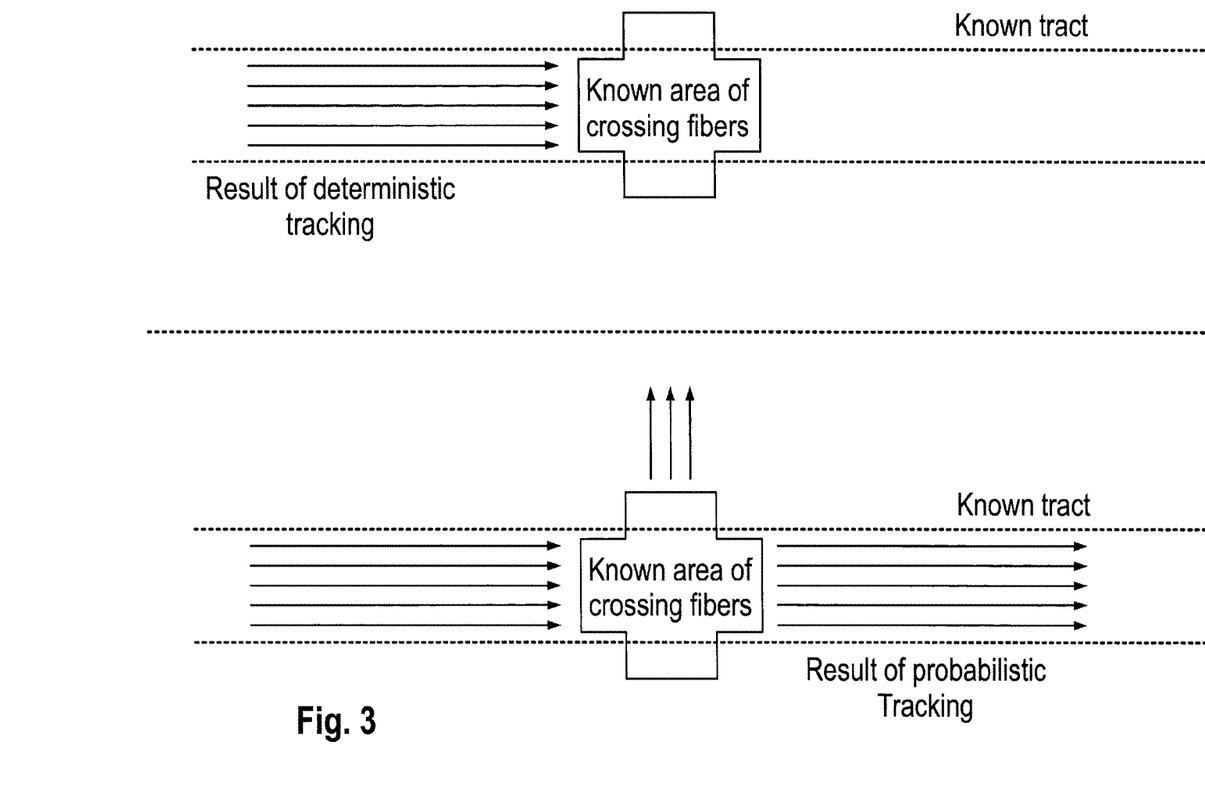
FIG. 3 is an illustration of a stepwise procedure, wherein deterministic tracts terminate at the crossing area, while probabilistic parameters are adapted until a known tract through a crossing region is captured; these settings are saved/utilized.

At first, the crossing is not going to be observable as the majority of fibres/tracking are going to terminate at the crossing zone itself (where the tensors might become indeterminate/more spherical). Now the probabilistic tractography settings are progressively relaxed until the crossing becomes observable (the trackings make it through the crossing zone and terminate in the target area). This is also illustrated by FIG. 3 which shows the results of probabilistic fibre tracking as compared to deterministic fibre tracking.

In step S3 the settings are then utilized to track the earlier deterministically tracked canonical white matter regions and the probability values within the earlier saved visitation mask (see FIG. 3) are captured.

In step S4 the probability value distribution within visitation masks is received for tracts that are for example long/short, curved/not curved.

Now that any probabilistic tracking result (the resulting probability field) can be scaled on the basis of a comparable tract (in terms of length and maximum curvature) and the results put into perspective, it becomes clear whether the tracking is more probable or less probable then a comparable tract tracked under identical parameter conditions.

This method can be further refined by employing Random-Field-Theory methods known from functional magnetic resonance imaging (fMRI) data analysis. By comparing the obtained probability fields from a novel exploratory tractography with probability fields of comparable smoothness (three-dimensional smoothness of the probability field, describing e.g. whether there are hotspots/blobs with highly probable cores and decreasing probabilities towards the edges or is it a rugged field with chaotic probability values), methods can be employed to determine the Euler-characteristics and establish at what probability thresholding areas can be identified which have high probabilities which do not appear in spatial groups (corresponding to tracts) due to random variations in comparable probability fields (see Family-Wise-Error control procedures in e.g. SPM fMRI).

A parameter boundary is established that allows at the conservative end probabilistic tractography which reproduces safe deterministic results and at the liberal end allows for tracking crossing fibre configurations without being arbitrary. By utilizing probability histograms from probabilistic tractography steps obtained under fixed conditions, new probabilistic histograms from exploratory probabilistic tractography can be scaled and visualized in direct comparison.

An advantage of the invention is that one can receive knowledge of standard anatomical tracts in the human brain, a scheme for the stepwise relaxation of probabilistic tractography parameters and a system for storing progressively obtained probability fields for subsequent intra-subject intra-dataset comparisons.

The invention relates for example to the following embodiments A and B of the above-described method:

EMBODIMENT A

A method for intra-subject/session intra-dataset calibration of tracking parameters and/or for obtaining probability scaling information for interpretation of results, comprising:
  identification of known anatomical zones in cerebral white matter;
  identification/acquisition of information regarding features of such zones;
  iterative relaxation of tracking parameters until known crossings are overcome and/or complex tracts are reconstructed utilization of probability histograms to aid interpretation of probabilistic results within known/identified feature classes of fibre tracts.

EMBODIMENT B

The method follows this routine:
The DTI data is pre-processed so as to result in a tensor, glyph or other representation of the white matter directionality on voxel level, for this there is a Universal Atlas Registration where the Atlas is multi-modally fused with multiple datasets and anatomical information from T1-like MR scans is combined with the DTI data itself by means of an elastic image fusion inverting the EPI-style geometric distortions present in the DTI-sequence, to optimally match the fine tissue information of the T1 image onto the DTI tensor workspace.

From the elastic fusion with the universal atlas areas, objects, surfaces and seed points stored in the Universal Atlas are transferred into the dataset, post-processing steps might be activated at this point that refine the image segmentation further.

A tissue class segmentation is performed in the patient dataset to identify which parts of the image are white matter, again through the multiple registration and fusion links multi-modal information can be combined in this step.

The white matter is analyzed by e.g. a shape fitting method to find paired or unpaired (in both hemispheres present or not) parts of expectable cerebral white matter bundles (such as the cortico-spinal tracts etc.).

Alternative methods include an identification of known connectome backbone structures through intra-cerebral deterministic fibre tracking from canonical seed structures (e.g. track the bundle from motor cortex left to brainstem, etc. until all major white matter bundles of the brain have been tracked).

Identified white matter zones are sorted according to the factors length, maximum curvature and probability to contain crossing fibres based on known anatomy (this information is in the Universal Atlas).

The parameters of a probabilistic tractography approach are calibrated by re-tracking the known white matter bundles so as to arrive at parameters that successfully penetrate crossing fibre configurations to faithfully reconstruct known fibre crossings as well as other structures such as strongly curved areas (optic radiation) etc.

The resulting probability histograms are stored.
The identified optimal probabilistic tractography parameters which could be used to successfully track through uncertain fibre configurations are utilized by the user.

The resulting probability histogram is compared with the saved probability histogram of a white matter zone, which is comparable in terms of number of seed voxels, length, expected maximum curvature and expected probability to contain crossing fibres.

If the abnormality detection of the universal atlas points to an abnormality within or in the vicinity of the target bundle, the probabilistic parameters can be relaxed appropriately as if crossing fibres were to be expected The comparison can be used for a calibration of heatmap probability visualizations or description of the probability in one tract by illustrating the earth-movers-distance between the two probability histograms of the reference bundle and the bundle in question.

The invention claimed is:

1. A medical system for determining information describing a probable position of a neural fibre in at least part of a patient's brain, the system comprising:
at least one computer having at least one processor that executes instructions stored on a computer readable storage medium to determine information describing a probable position of the neural fibre in the at least one part of the patient's brain, the instructions operable to cause the computer to:
acquire, at the at least one processor, patient-specific medical image data describing the at least part of the brain of the patient;
acquire, at the at least one processor, atlas data defining an image-based model of at least part of a human brain;
determine, by the at least one processor and based on the patient-specific medical image data and the atlas data, seed region data describing seed regions in the patient-specific medical image data in which the ends of neural fibres of the patient's brain may be located,
wherein the seed region data is determined by determining a transformation between the atlas data and the patient-specific medical image data, and determining the position of white brain matter in the patient-specific medical image data based on the transformation, wherein the seed regions are at least two spatially disjunct and individually coherent seed regions and are constituted by white brain matter;
determine, by the at least one processor and based on the patient-specific medical image data and the seed region data, neural fibre tract data describing a plurality of potential tracts which a specific neural fibre may take through the patient's brain;
determine, by the at least one processor and based on the atlas data and the neural fibre tract data, a figure of merit for each one of a plurality of potential tracts;
wherein the positions of a plurality of spatially disjunct and individually coherent regions of white brain matter are determined in the patient-specific medical image data based on the transformation, and
wherein the coherent regions of white brain matter are sorted according to the geometric properties of model neural fibre tracts in the image-based model connecting regions of white brain matter and according to the probability of the respective model neural fibre tracts to contain fibre crossings, and
wherein regions of white brain matter having a high probability for containing a fibre crossing are selected as the seed regions for determining the neural fibre tract data.

2. A computer-implemented method of determining a probable position of a neural fibre in at least part of a patient's brain, the method comprising executing, by at least one processor of at least one computer, steps of:
acquiring, at the at least one processor, patient-specific medical image data describing the at least part of the brain of the patient;
acquiring, at the at least one processor, atlas data defining an image-based model of at least part of a human brain;
determining, by the at least one processor and based on the patient-specific medical image data and the atlas data, seed region data describing seed regions in the patient-specific medical image data in which the ends of neural fibres of the patient's brain may be located, wherein the seed region data is determined by determining a transformation between the atlas data and the patient-specific medical image data, and determining the position of white brain matter in the patient-specific medical image data based on the transformation, wherein the seed regions are at least two spatially disjunct and individually coherent seed regions and are constituted by white brain matter;
determining, by the at least one processor and based on the patient-specific medical image data and the seed region data, neural fibre tract data describing a plurality of potential tracts which a specific neural fibre may take through the patient's brain;
determining, by the at least one processor and based on the atlas data and the neural fibre tract data, a figure of merit for each one of the potential tracts ($T_1$, $T_2$, $T_3$), wherein the positions of a plurality of spatially disjunct and individually coherent regions of white brain matter are determined in the patient-specific medical image data based on the transformation, and wherein the coherent regions of white brain matter are sorted according to the geometric properties of model neural fibre tracts in the image-based model connecting regions of white brain matter and according to the probability of the respective model neural fibre tracts to contain fibre crossings, and wherein regions of white brain matter having a high probability for containing a fibre crossing are selected as the seed regions for determining the neural fibre tract data.

3. The method according to claim 2, wherein the patient-specific medical image data is suitable for identifying neural fibres in the brain of the patient and is medical image data which has been generated at least partly by diffusion tensor imaging.

4. The method according to claim 2, wherein the atlas data comprises tissue class information describing the image appearance of specific body tissue in the imaging modality which is used to generate the patient-specific medical image information.

5. The method according to claim 2, wherein the transformation is determined, by the at least one processor, by performing an image fusion between the atlas data and the patient-specific medical image data.

6. The method according to claim 5, wherein the transformation is determined, by the at least one processor, by determining the position of white brain matter in the patient specific medical image data based on the transformation, wherein the seed regions are constituted by white brain matter.

7. The method according to claim 6, wherein the atlas data comprises tissue class information describing the image appearance of specific body tissue in the imaging modality which is used to generate the patient-specific medical image information and wherein the position of the white brain matter in the image-based model is determined by segmenting the image-based model for tissue class information defining white brain matter.

8. The method according to claim 2, wherein the neural fibre tract data is determined, by the at least one processor, by selecting exactly one of the seed regions as a start region and applying a random walk algorithm to the patient-specific medical image data which generates a plurality of random walks, wherein each random walk out of the plurality of random walks is designed to start at the start region and to lead to another one of the seed regions which serves as a desired end region for the random walk.

9. The method according to claim 8, wherein the initial values of the random walk algorithm are determined, by the at least one processor, based on the sorting of the coherent regions, wherein the initial values of the random walk algorithm are determined, by the at least one processor, so as to optimally represent the ideal conditions under which said reference coherent region was optimally reconstructed.

10. The method according to claim 8, wherein the random walk algorithm is initiated at a specific position $s\_0$ in the start region with a predetermined step size d, and wherein every direction $v\_i$ in which each one of the N−1 total steps of the random walk proceeds from the current position $s\_i$, where $i=0, 1, 2, \ldots, N$; and N−1 is the length of the random walk currently considered by the random walk algorithm and is determined, by the at least one processor, based on the patient-specific medical image data determined from the patient-specific medical image data for the current position $s\_i$.

11. The method according to claim 10, wherein every direction in which the random walk proceeds is determined based on determining a probability of that direction being a valid direction for propagating the random walk, the probability being determined based on the result of an analysis of the geometry of at least one of size and shape, of a diffusion tensor determined from the patient-specific medical image data for the current position $s\_i$.

12. The method according to claim 9, wherein each one of the plurality of random walks which does not end in the end region is excluded from further data processing and wherein each one of the plurality of random walks which ends in the end region is considered for further data processing.

13. The method according to claim 8, wherein the atlas data comprises fibre tract model information about the position of model neural fibre tracts in the image-based model, and wherein the fibre tract model information is compared, based on at least one physical parameter of pre-tracked white brain matter structures such as their length, curvedness, anatomical similarity, to the corresponding random-walk based fibre.

14. The method according to claim 12, wherein the curvature of the core of at least one of the model neural fibre tracts in the image-based model is the curvature with respect to a non-curved virtual line between the end points of the tract, and wherein the curvature of the random walks is a calculated similarity with respect to the non-curved virtual line between the target termination area of the random walks.

15. The method of claim 9 wherein the sorting of coherent regions is based on the sorting of physical parameters of pre-tracked white brain matter structures such as their length, curvedness, anatomical similarity and/or probability for containing crossing fibres.

16. The method according to claim 2, further comprising determining, by the at least one processor, based on the figure of merit, the potential fibre tract as being a fibre tract which is suitable for planning a medical procedure which the patient shall be subjected to.

17. A non-transitory computer-readable program storage medium storing a program having instructions, which, when executed by at least one processor of at least one computer, causes the at least one computer to determine information describing a probable position of a neural fibre in at least part of a patient's brain, the instructions causing the at least one computer to perform the steps of:
acquiring, at the at least one processor, patient-specific medical image data describing the at least part of the brain of the patient;
acquiring, at the at least one processor, atlas data defining an image-based model of at least part of a human brain;
determining, by the at least one processor and based on the patient-specific medical image data and the atlas data, seed region data describing seed regions in the patient-specific medical image data in which the ends of neural fibres of the patient's brain may be located, wherein the seed region data is determined by determining a transformation between the atlas data and the patient-specific medical image data, and determining the position of white brain matter in the patient-specific medical image data based on the transformation, wherein the seed regions are at least two spatially disjunct and individually coherent seed regions and are constituted by white brain matter;
determining, by the at least one processor and based on the patient-specific medical image data and the seed region data, neural fibre tract data describing a plurality of potential tracts which a specific neural fibre may take through the patient's brain;
determining, by the at least one processor and based on the atlas data and the neural fibre tract data, a figure of merit for each one of the potential tracts, wherein the positions of a plurality of spatially disjunct and individually coherent regions of white brain matter are determined in the patient-specific medical image data based on the transformation, and wherein the coherent regions of white brain matter are sorted according to the geometric properties of model neural fibre tracts in the image-based model connecting regions of white brain matter and according to the probability of the respective model neural fibre tracts to contain fibre crossings, and wherein regions of white brain matter having a high probability for containing a fibre crossing are selected as the seed regions for determining the neural fibre tract data.

* * * * *